US00PP17547P2

(12) United States Plant Patent
de Winter

(10) Patent No.: US PP17,547 P2
(45) Date of Patent: Apr. 3, 2007

(54) ***ECHINACEA* PLANT NAMED 'ALASKA'**

(50) Latin Name: *Echinacea purpurea*
Varietal Denomination: Alaska

(75) Inventor: Dirk de Winter, Obdam (NL)

(73) Assignee: Compass Plants B.V., Hillegom (NL)

( * ) Notice: Subject to any disclaimer, the term of this patent is extended or adjusted under 35 U.S.C. 154(b) by 27 days.

(21) Appl. No.: 11/151,757

(22) Filed: Jun. 14, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Echinacea* plant named 'Alaska', characterized by its compact growth habit; rapid growth rate; freely and uniform flowering habit; white-colored ray florets; long and continuous flowering period; and good garden performance.

1 Drawing Sheet

Botanical designation: *Echinacea purpurea.*
Cultivar denomination: 'Alaska'.

BACKGROUND OF THE INVENTION

The present Invention relates to a new and distinct cultivar of *Echinacea* plant, botanically known as *Echinacea purpurea,* and hereinafter referred to by the name 'Alaska'.

The new *Echinacea* is a product of a planned breeding program conducted by the Inventor in Obdam, The Netherlands. The objective of the breeding program is to develop new compact *Echinacea* cultivars with attractive inflorescence coloration.

The new *Echinacea* originated from a cross-pollination in 1999 of two unnamed selections of *Echinacea purpurea,* not patented. The new *Echinacea* was discovered and selected as a single flowering plant by the Inventor in a controlled environment in Obdam, The Netherlands in 2001 from the resultant progeny of the cross-pollination. The new *Echinacea* was selected on the basis of its compact growth habit, attractive ray and disc floret coloration and attractive inflorescence coloration.

Asexual reproduction of the new *Echinacea* by divisions was first conducted in Obdam, The Netherlands in 2002. Since then, asexual reproduction by divisions has shown that the unique features of this new *Echinacea* are stable and reproduced true to type in successive generations.

SUMMARY OF THE INVENTION

The cultivar Alaska has not been observed under all possible environmental conditions. The phenotype may vary somewhat with variations in environment such as temperature and light intensity without, however, any variance in genotype.

The following traits have been repeatedly observed and are determined to be the unique characteristics of 'Alaska'. These characteristics in combination distinguish 'Alaska' as a new and distinct *Echinacea:*

1. Compact growth habit.
2. Rapid growth rate.
3. Freely and uniform flowering habit.

4. White-colored ray florets.
5. Long and continuous flowering period.
6. Good garden performance.

Plants of the new *Echinacea* differ primarily from plants of the parent selections in plant height, inflorescence form and ray floret coloration.

Plants of the new *Echinacea* can be compared to plants of the *Echinacea* cultivar Kim's Mop Head, disclosed in U.S. Plant Pat. No. 13,560. In side-by-side comparisons conducted in Obdam, The Netherlands, plants of the new *Echinacea* differed from plants of the cultivar Kim's Mop Head in the following characteristics:

1. Plants of the new *Echinacea* were more compact than plants of the cultivar Kim's Mop Head.
2. Ray florets of plants of the new *Echinacea* were more horizontal-orientated than ray florets of plants of the cultivar Kim's Mop Head.

Plants of the new *Echinacea* can also be compared to plants of the *Echinacea* cultivar Kim's Knee High, disclosed in U.S. Plant Pat. No. 12,242. In side-by-side comparisons conducted in Obdam, The Netherlands, plants of the new *Echinacea* differed from plants of the cultivar Kim's Knee High in the following characteristics:

1. Ray florets of plants of the new *Echinacea* were more horizontally-orientated than ray florets of plants of the cultivar Kim's Knee High.
2. Plants of the new *Echinacea* and the cultivar Kim's Knee High differed in ray floret color as plants of the cultivar Kim's Knee High had purple-colored ray florets.

BRIEF DESCRIPTION OF THE PHOTOGRAPH

The accompanying colored photograph illustrates the overall appearance of the new *Echinacea* showing the colors as true as it is reasonably possible to obtain in colored reproductions of this type. Colors in the photograph may differ from the color values cited in the detailed botanical description which accurately describe the colors of the new *Echinacea.* The photograph comprises a side perspective view of a typical flowering plant of 'Alaska' grown in an outdoor nursery.

DETAILED BOTANICAL DESCRIPTION

The aforementioned photograph and following observations and measurements describe plants grown in Obdam, The Netherlands, in an outdoor nursery under full sun conditions during the summer. When the plants were about one year old, the photograph and the observations and measurements were taken. Plants used for the detailed description were grown in 15-cm containers. During the production of the plants, day temperatures ranged from 5 to 20° C. and night temperatures ranged from 2 to 12° C. Color references are made to The Royal Horticultural Society Colour Chart, 2001 Edition, except where general terms of ordinary dictionary significance are used.

Botanical classification: *Echinacea purpurea* cultivar Alaska.

Parentage:

*Female, or seed, parent.*—Unnamed selection of *Echinacea purpurea,* not patented.

*Male, or pollen, parent.*—Unnamed selection of *Echinacea purpurea,* not patented.

Propagation:

*Type.*—By divisions.

*Time to initiate roots, summer.*—About three weeks at 18° C.

*Time to initiate roots, winter.*—About five weeks at 18° C.

*Time to produce a rooted plant, summer.*—About four weeks at 18° C.

*Time to produce a rooted plant, winter.*—About six weeks at 18° C.

*Root description.*—Fibrous; well-branched.

Plant description:

*Appearance.*—Perennial herbaceous container and garden plant. Upright and compact plant habit; inverted triangle. Freely basally branching; Moderately vigorous; rapid growth rate.

*Plant height.*—About 50 cm.

*Plant width or area of spread.*—About 40 cm.

*Basal branches.*—Length: About 45 cm. Diameter: About 4 mm. Aspect: Mostly upright. Strength: Strong. Texture: Smooth. Color: 145A.

*Foliage description.*—Arrangement: Alternate; single. Length: About 10 to 18 cm. Width: About 4 to 6 cm. Shape: Lanceolate. Apex: Acuminate. Base: Attenuate. Margin: Serrate. Venation pattern: Parallel. Texture, upper and lower surfaces: Pubescent; scabrous. Color: Developing and fully expanded foliage, upper surface: 137B. Developing and fully expanded foliage, lower surface: 138B. Venation, upper surface: 145A. Venation, lower surface: 146C. Petiole: Length: About 2 cm. Diameter: About 5 mm. Texture, upper and lower surfaces: Smooth. Color, upper surface: 145A. Color, lower surface: 146C.

Inflorescence description:

*Appearance.*—Terminal inflorescences held mostly above and beyond the foliage on strong peduncles and held mostly upright. Composite inflorescence form, radially symmetrical; oblanceolate-shaped ray florets; disc florets massed at the center; ray and disc florets develop acropetally on the receptacle. Inflorescences persistent.

*Time of flowering.*—Long flowering period; plants flower freely during the early summer and continue to flower continuously through the fall in The Netherlands.

*Postproduction longevity.*—Inflorescences maintain good color and substance for about three or four weeks on the plant.

*Quantity of inflorescences.*—One inflorescence per stem; about 40 inflorescences in flower at one time per plant.

*Fragrance.*—None detected.

*Inflorescence bud.*—Length: About 5 cm. Diameter: About 7.5 cm. Shape: Roughly spherical. Color: 157C to 143A.

*Inflorescence size.*—Diameter: About 15 cm. Depth (height): About 5 cm. Disc diameter: About 5 cm.

*Ray florets.*—Length: About 5 cm. Width: About 1.5 cm. Shape: Oblanceolate. Apex: Obtuse, acute or emarginate. Base: Attenuate. Margin: Entire. Texture, upper and lower surfaces: Smooth. Orientation: Initially upright then roughly horizontal, perpendicular to the peduncle. Number of ray florets per inflorescence: About 30 in a single whorl. Color: When opening and fully opened, upper surface: 155B; towards the base, 143B. When opening, lower surface: 155D; towards the base, 144A.

*Disc florets.*—Shape: Elongated. Apex: Five-pointed; acute. Length: About 2 cm. Width: About 2 mm. Number of disc florets per inflorescence: Numerous. Color, immature: Close to 147A. Color, mature: Apex: Close to N144A. Mid-section: Close to 144A. Base: Close to 155D.

*Phyllaries.*—Quantity per inflorescence: About 25 to 58. Length: About 2 cm. Diameter: About 5 mm. Shape: Lanceolate. Apex: Acute. Base: Fused to receptacle. Margin: Entire. Texture, upper and lower surfaces: Pubescent. Color, upper and lower surfaces: 143A.

*Reproductive organs.*—Androecium: Present on disc florets only. Stamen number: About six per floret; basifixed. Anther shape: Narrowly oblong. Anther length: About 2 mm. Anther color: 153A. Pollen amount: Moderate. Pollen color: 7B. Gynoecium: Present on both ray and disc florets. Pistil number: One per floret. Pistil length: About 5 mm. Stigma shaped: Two-parted. Stigma color: Close to 6A. Style length: About 4 mm. Style color: Close to 155D. Ovary color: 145A.

*Seed.*—Length: Less than 5 mm. Diameter: Less than 2 mm. Color: Medium tan.

Disease/pest resistance: Resistance to pathogens and pests common to *Echinaceas* has not been observed on plants grown under outdoor conditions.

Garden performance: Plants of the new *Echinacea* have been observed to have good garden performance and to tolerate wind and rain. Plants of the new *Echinacea* have been observed to be winter hardy in The Netherlands.

It is claimed:

1. A new and distinct cultivar of *Echinacea* plant named 'Alaska', as illustrated and described.

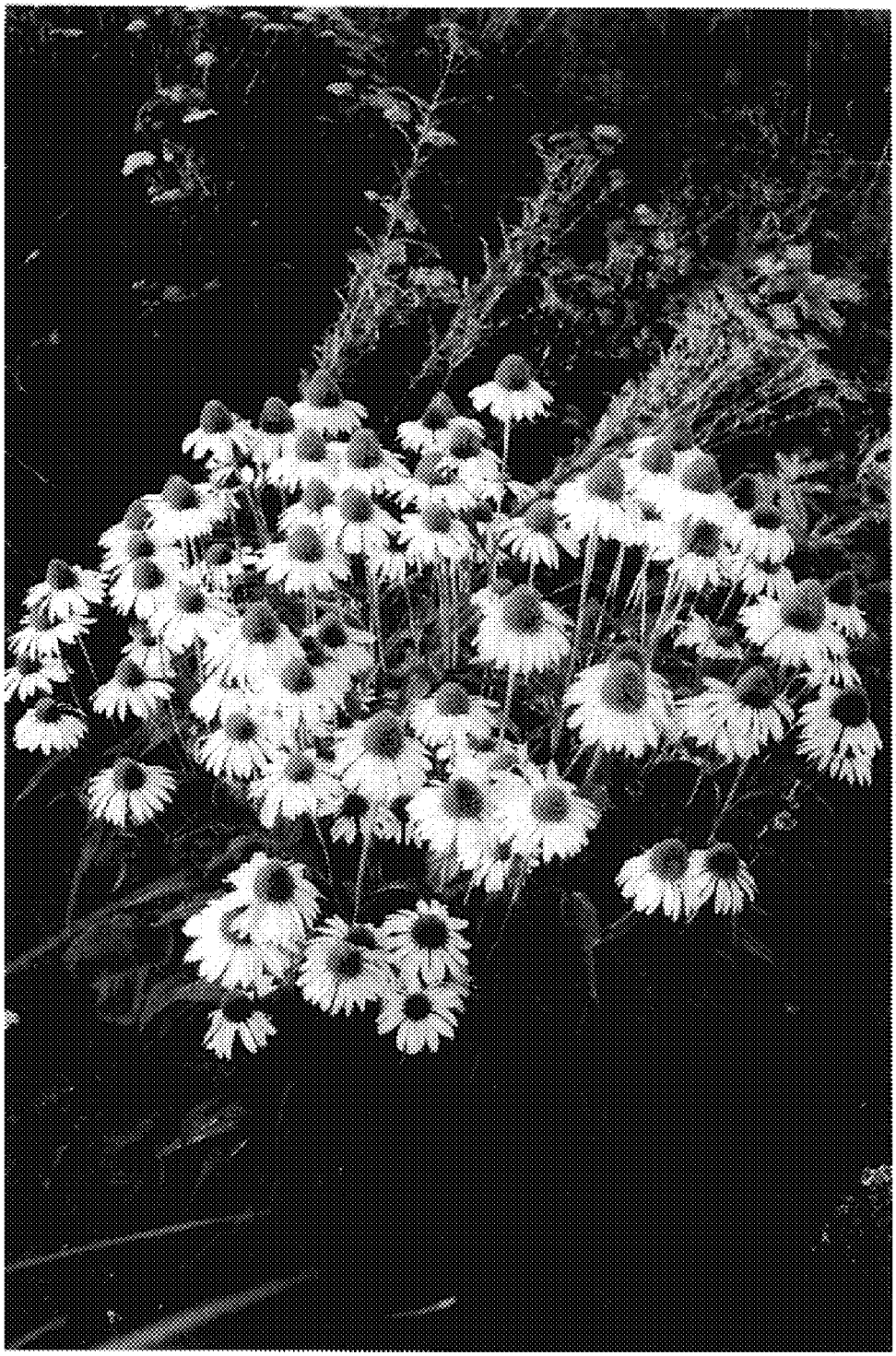

* * * * *